United States Patent
Matsumura et al.

(10) Patent No.: US 11,377,504 B2
(45) Date of Patent: Jul. 5, 2022

(54) ANTIBODY BENEFICIAL FOR TREATMENT OF SOLID TUMORS, ANTIBODY-DRUG CONJUGATE, AND CANCER DRUG INCLUDING SAME

(71) Applicants: National Cancer Center Japan, Chuo-ku (JP); RIN Institute Inc., Chuo-ku (JP)

(72) Inventors: Yasuhiro Matsumura, Chiba (JP); Masahiro Yasunaga, Chiba (JP); Shinji Saijo, Chiba (JP); Ryo Tsumura, Chiba (JP)

(73) Assignees: National Cancer Center Japan, Chuo-ku (JP); RIN Institute Inc., Chuo-ku (JP)

( * ) Notice: Subject to any disclaimer, the term of this patent is extended or adjusted under 35 U.S.C. 154(b) by 77 days.

(21) Appl. No.: 16/760,539

(22) PCT Filed: Oct. 29, 2018

(86) PCT No.: PCT/JP2018/040017
§ 371 (c)(1),
(2) Date: Apr. 30, 2020

(87) PCT Pub. No.: WO2019/087994
PCT Pub. Date: May 9, 2019

(65) Prior Publication Data
US 2021/0221911 A1   Jul. 22, 2021

(30) Foreign Application Priority Data
Oct. 30, 2017   (JP) ............................. JP2017-208907

(51) Int. Cl.
| | |
|---|---|
| *C07K 16/36* | (2006.01) |
| *A61K 47/68* | (2017.01) |
| *A61P 35/00* | (2006.01) |
| *G01N 33/68* | (2006.01) |
| *A61K 39/00* | (2006.01) |

(52) U.S. Cl.
CPC .......... *C07K 16/36* (2013.01); *A61K 47/6843* (2017.08); *A61P 35/00* (2018.01); *G01N 33/6854* (2013.01); *A61K 2039/505* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2003/0119075 A1 | 6/2003 | Kirchhofer et al. |
| 2004/0044187 A1 | 3/2004 | Sato et al. |
| 2004/0229301 A1 | 11/2004 | Wang |
| 2011/0300156 A1 | 12/2011 | Verploegen et al. |
| 2012/0237528 A1 | 9/2012 | Almagro et al. |
| 2013/0123471 A1 | 5/2013 | Yang et al. |
| 2016/0333113 A1 | 11/2016 | Matsumura et al. |

FOREIGN PATENT DOCUMENTS

| | | | |
|---|---|---|---|
| EP | 1 069 185 A1 | 1/2001 | |
| EP | 2 567 982 A1 | 3/2013 | |
| EP | 3 159 358 A1 | 4/2017 | |
| JP | 2003-527861 A | 9/2003 | |
| JP | 2007-525944 A | 9/2007 | |
| JP | 2012-511314 A | 5/2012 | |
| JP | 2013-534406 A | 9/2013 | |
| JP | 2014-509856 A | 4/2014 | |
| JP | WO2015/115656 A1 | 8/2015 | |
| WO | WO 99/51743 A1 | 10/1999 | |
| WO | WO 01/70984 A2 | 9/2001 | |
| WO | WO 2004/094475 A2 | 11/2004 | |
| WO | WO-2010066803 A2 * | 6/2010 | ............. A61P 15/08 |

OTHER PUBLICATIONS

Janeway et al., Immunobiology, 3rd edition, 1997 Garland Publishing Inc., pp. 3:1-3:11.*
Rudikoff et al., Proc Natl Acad Sci USA. Mar. 1982;79(6):1979-83.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Yoshikatsu Koga et al., "Antitumor Effect of Antitissue Factor Antibody—MMAE Conjugate in Human Pancreatic Tumor Xenografts," International Journal of Cancer, vol. 137, pp. 1457-1466, 2015.
Supplementary European Search Report dated Jul. 5, 2021 in European Patent Application No. 18873165.7, 18 pages.
Stephen I. Rudnick, et al., "Affinity and Avidity in Antibody-Based Tumor Targeting", Cancer Biotherapy and Radiopharmaceuticals, XP55069540, vol. 24 No. 2, Apr. 2009, pp. 155-161.
Ryo Tsumura, et al., "Influence of the dissociation rate constant on the intra-tumor distribution of antibody-drug conjugate against tissue factor", Journal of Controlled Release, XP085438381, vol. 284, Jun. 2018, pp. 49-56.
International Search Report dated Jan. 29, 2019 in PCT/JP2018/040017 filed on Oct. 29, 2018, 4 pages.

(Continued)

*Primary Examiner* — Michael Szperka
(74) *Attorney, Agent, or Firm* — Oblon, McClelland, Maier & Neustadt, L.L.P.

(57) ABSTRACT

The present invention provides an antibody beneficial for treatment of a solid tumor, an antibody-drug conjugate thereof, and an anticancer agent comprising these. The present invention provides, for example, an antibody that binds to tissue factor or an antigen-binding fragment thereof, wherein the antibody has a dissociation rate constant kd of $5 \times 10^{-4}$ $s^{-1}$ or more and an association rate constant Ka of $1 \times 10^4$ $M^{-1}$ $s^{-1}$ or more.

4 Claims, 1 Drawing Sheet
Specification includes a Sequence Listing.

(56) References Cited

OTHER PUBLICATIONS

Koga et al., "Antitumor effect of antitissue factor antibody—MMAE conjugate in human pancreatic tumor xenografts," International Journal of Cancer, vol. 137, pp. 1457-1466, 2015.
Extended European Search Report dated Oct. 22, 2021 in European Patent Application No. 18873165.7, 21 pages.
Greg M. Thurber, Chapter 16: "Tumor Effect Site Pharmacokinetics: Mechanisms and Impact on Efficacy" In: Honghui Zhou and Frank-Peter Theil: ADME and Translational Pharmacokinetixcs/Pharmacodynamics of Therapeutic Proteins Applications in Drug Discovery and Development, XP002804392, 2016, 30 pages.
Greg M. Thurber, et al., "Antibody Tumor Penetration: Transport Opposed by Systemic and Antigen-Mediated Clearance" Advanced Drug Delivery Reviews, Elsevier, Amsterdam, NL, vol. 60, No. 12. XP022851270, Sep. 15. 2008, pp. 1421-1434.
Ryo Tsumura, et al., "The Dissociation Constant Rate of ADC would be an Important Factor for Antitumor Activity In Vivo", Cancer Research, American Association For Cancer Research, US, vol. 77, No. 13, XP002804391, Supplement 1, Jul. 1, 2017, 4 pages.
"Kinetics, Thermodynamics, and Ligand Efficiency Metrics in Drug Discovery" In: Comprehensive Medicinal Chemistry III Elsevier, vol. 2, XP055849124, Jan. 1, 2017, pp. 180-211.
Yu Tang, et al., "Modeling Pharmacokinetics and Pharmacodynamics of Therapeutic Antibodies: Progress, Challenges, and Future Directions" Pharmaceutics, vol. 13, No. 3, XP055848599, Mar. 21, 2021, pp. 1-28.

* cited by examiner

SEQUENCE LISTING

<160> NUMBER OF SEQ ID NOS: 13

<210> SEQ ID NO 1
<211> LENGTH: 116
<212> TYPE: PRT
<213> ORGANISM: Artificial Sequence
<220> FEATURE:
<223> OTHER INFORMATION: 1084 heavy chain variable region

<400> SEQUENCE: 1

Gln Val Gln Leu Lys Glu Ser Gly Pro Gly Leu Val Gln Pro Ser Gln
1               5                   10                  15

Thr Leu Ser Leu Thr Cys Ile Val Ser Gly Phe Ser Leu Thr Asn Tyr
            20                  25                  30

Asn Val His Trp Val Arg Gln Pro Ala Gly Ala Gly Leu Glu Trp Met
        35                  40                  45

Gly Val Ile Trp Thr Asp Gly Lys Thr Asp Tyr Asn Ser Thr Leu Gln
    50                  55                  60

Ser Arg Leu Ser Ile Ser Arg Asp Thr Ser Lys Ser Gln Val Phe Leu
65                  70                  75                  80

Lys Met Asn Ser Leu Gln Ala Glu Asp Ile Ala Thr Tyr Tyr Cys Ala
                85                  90                  95

Arg Asp Trp Asp Thr Gly Phe Asp Tyr Trp Gly Gln Gly Val Met Val
            100                 105                 110

Thr Val Ser Ser
        115

<210> SEQ ID NO 2
<211> LENGTH: 5
<212> TYPE: PRT
<213> ORGANISM: Artificial Sequence
<220> FEATURE:
<223> OTHER INFORMATION: 1084 HCDR1

<400> SEQUENCE: 2

Asn Tyr Asn Val His
1               5

<210> SEQ ID NO 3
<211> LENGTH: 16
<212> TYPE: PRT
<213> ORGANISM: Artificial Sequence
<220> FEATURE:
<223> OTHER INFORMATION: 1084 HCDR2

<400> SEQUENCE: 3

Val Ile Trp Thr Asp Gly Lys Thr Asp Tyr Asn Ser Thr Leu Gln Ser
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: 1084 HCDR3

<400> SEQUENCE: 4

Asp Trp Asp Thr Gly Phe Asp Tyr
1               5

<210> SEQ ID NO 5
<211> LENGTH: 106
<212> TYPE: PRT

<213> ORGANISM: Artificial Sequence
<220> FEATURE:
<223> OTHER INFORMATION: 1084 light chain variable region

<400> SEQUENCE: 5

```
Asp Ile Lys Met Thr Gln Ser Pro Ser Leu Ser Ala Ser Leu Gly
1               5                   10                  15

Glu Arg Val Thr Ile Ser Cys Arg Ala Ser Glu Asn Ile Asn Asn Ile
            20                  25                  30

Leu Ala Trp Tyr Gln Lys Lys Glu Asp Gly Ser Val Lys Leu Leu Ile
        35                  40                  45

His Tyr Thr Ser Asn Leu Gln Ser Gly Val Pro Ser Arg Phe Ser Gly
    50                  55                  60

Ser Gly Ser Gly Lys Asp Tyr Ser Leu Thr Ile Ser Gly Leu Glu Ser
65                  70                  75                  80

Glu Asp Ile Ala Thr Tyr Tyr Cys Gln Gln Ala Tyr Thr Pro Tyr Ala
                85                  90                  95

Phe Gly Ala Gly Thr Lys Leu Glu Leu Lys
            100                 105
```

<210> SEQ ID NO 6
<211> LENGTH: 11
<212> TYPE: PRT
<213> ORGANISM: Artificial Sequence
<220> FEATURE:
<223> OTHER INFORMATION: 1084 LCDR1

<400> SEQUENCE: 6

```
Arg Ala Ser Glu Asn Ile Asn Asn Ile Leu Ala
1               5                   10
```

<210> SEQ ID NO 7
<211> LENGTH: 7
<212> TYPE: PRT
<213> ORGANISM: Artificial Sequence
<220> FEATURE:
<223> OTHER INFORMATION: 1084 LCDR2

<400> SEQUENCE: 7

```
Tyr Thr Ser Asn Leu Gln Ser
1               5
```

<210> SEQ ID NO 8
<211> LENGTH: 8
<212> TYPE: PRT
<213> ORGANISM: Artificial Sequence
<220> FEATURE:
<223> OTHER INFORMATION: 1084 LCDR3

<400> SEQUENCE: 8

```
Gln Gln Ala Tyr Thr Pro Tyr Ala
1               5
```

<210> SEQ ID NO 9
<211> LENGTH: 45
<212> TYPE: DNA
<213> ORGANISM: Artificial Sequence
<220> FEATURE:
<223> OTHER INFORMATION: Primer Mix, Long

<400> SEQUENCE: 9
ctaatacgac tcactatagg gcaagcagtg gtatcaacgc agagt     45

```
<210> SEQ ID NO 10
<211> LENGTH: 22
<212> TYPE: DNA
<213> ORGANISM: Artificial Sequence
<220> FEATURE:
<223> OTHER INFORMATION: Primer Mix, Short

<400> SEQUENCE: 10
ctaatacgac tcactatagg gc                                              22

<210> SEQ ID NO 11
<211> LENGTH: 28
<212> TYPE: DNA
<213> ORGANISM: Artificial Sequence
<220> FEATURE:
<223> OTHER INFORMATION: Reverse primer for heavy chain

<400> SEQUENCE: 11
tgtgcagacc ctcgtggacc acggagca                                        28

<210> SEQ ID NO 12
<211> LENGTH: 27
<212> TYPE: DNA
<213> ORGANISM: Artificial Sequence
<220> FEATURE:
<223> OTHER INFORMATION: Reverse primer for light chain

<400> SEQUENCE: 12
ccttaggagg gaagattgga aggagct                                         27

<210> SEQ ID NO 13
<211> LENGTH: 228
<212> TYPE: PRT
<213> ORGANISM: Artificial Sequence
<220> FEATURE:
<223> OTHER INFORMATION: Recombinant human tissue factor

<400> SEQUENCE: 13
```

Met Ser Gly Thr Thr Asn Thr Val Ala Ala Tyr Asn Leu Thr Trp Lys
 1               5                  10                  15

Ser Thr Asn Phe Lys Thr Ile Leu Glu Trp Glu Pro Lys Pro Val Asn
             20                  25                  30

Gln Val Tyr Thr Val Gln Ile Ser Thr Lys Ser Gly Asp Trp Lys Ser
         35                  40                  45

Lys Cys Phe Tyr Thr Thr Asp Thr Glu Cys Asp Leu Thr Asp Glu Ile
     50                  55                  60

Val Lys Asp Val Lys Gln Thr Tyr Leu Ala Arg Val Phe Ser Tyr Pro
 65                  70                  75                  80

Ala Gly Asn Val Glu Ser Thr Gly Ser Ala Gly Glu Pro Leu Tyr Glu
                 85                  90                  95

Asn Ser Pro Glu Phe Thr Pro Tyr Leu Glu Thr Asn Leu Gly Gln Pro
            100                 105                 110

Thr Ile Gln Ser Phe Glu Gln Val Gly Thr Lys Val Asn Val Thr Val
        115                 120                 125

Glu Asp Glu Arg Thr Leu Val Arg Arg Asn Asn Thr Phe Leu Ser Leu
    130                 135                 140

Arg Asp Val Phe Gly Lys Asp Leu Ile Tyr Thr Leu Tyr Tyr Trp Lys
145                 150                 155                 160

Ser Ser Ser Ser Gly Lys Lys Thr Ala Lys Thr Asn Thr Asn Glu Phe
                165                 170                 175

Leu Ile Asp Val Asp Lys Gly Glu Asn Tyr Cys Phe Ser Val Gln Ala

-continued

```
              180                 185                 190
Val Ile Pro Ser Arg Thr Val Asn Arg Lys Ser Thr Asp Ser Pro Val
        195                 200                 205

Glu Cys Met Gly Gln Glu Lys Gly Glu Phe Arg Glu Leu Glu His His
        210                 215                 220

His His His His
225
```

ANTIBODY BENEFICIAL FOR TREATMENT OF SOLID TUMORS, ANTIBODY-DRUG CONJUGATE, AND CANCER DRUG INCLUDING SAME

TECHNICAL FIELD

The present invention relates to an antibody beneficial for treatment of a solid tumor, an antibody-drug conjugate thereof, and an anticancer agent including these.

BACKGROUND ART

Tissue factor is expressed in many human cancer cells, and a positive correlation between expression thereof and grade of malignancy has been demonstrated by clinical research. An example of an antibody targeting the tissue factor is disclosed for example in Patent Literature 1. Furthermore, an antibody-drug conjugate (ADC) composed of an anti-tissue antibody and a cytotoxic agent is disclosed in Non Patent Literature 1.

CITATION LIST

Patent Literature

Patent Literature 1: WO2015/115656

Non Patent Literature

Non Patent Literature 1: "Antitumor effect of anti-tissue factor antibody-MMAE conjugate in human pancreatic tumor xenografts" Koga Y, Manabe S, Aihara Y, Sato R, Tsumura R, Iwafuji H, Furuya F, Fuchigami H, Fujiwara Y, Hisada Y, Yamamoto Y, Yasunaga M, Matsumura Y. Int. J. Cancer, 137, 1457-1466 (2015).

SUMMARY OF INVENTION

The present invention provides an antibody beneficial for treatment of a solid tumor, an antibody-drug conjugate thereof, and an anticancer agent including these.

The present inventors have studied antibodies against a tumor-specific antigen expressed in the solid tumor by comparing two antibodies having different dissociation rate constants, and have discovered that the antibody having a larger dissociation rate constant can penetrate into the inside of the solid tumor. The present inventors also have discovered that an antibody having a smaller dissociation constant KD but has a larger dissociation rate constant kd (i.e., an antibody that easily dissociates from the antigen) has a stronger antitumor effect than an antibody having a smaller Kd (i.e., an antibody that does not easily dissociate from the antigen).

The present invention provides the following embodiments.

(1) An antibody that binds to tissue factor, or an antigen-binding fragment thereof, wherein the antibody has a dissociation rate constant kd of $5 \times 10^{-4}$ $s^{-1}$ or more and an association rate constant Ka of $1 \times 10^4$ $M^{-1}$ $s^{-1}$ or more.

(2) An antibody that binds to tissue factor, or an antigen-binding fragment thereof, wherein the antibody comprises:
a heavy chain variable region comprising CDRs 1 to 3 having an amino acid sequence of SEQ ID NOs: 2 to 4, respectively; and
a light chain variable region comprising CDRs 1 to 3 having an amino acid sequence of SEQ ID NOs: 6 to 8, respectively.

(3) The antibody according to the above described (2), or an antigen-binding fragment thereof, wherein the antibody comprises:
a heavy chain variable region having an amino acid sequence of SEQ ID NO: 1; and
a light chain variable region having an amino acid sequence of SEQ ID NO: 5.

(4) An antibody that binds to tissue factor, or an antigen-binding fragment thereof, wherein the antibody mutually competes with the antibody according to the above (2) or (3) for binding to tissue factor.

(5) A pharmaceutical composition for use in treating cancer, comprising the antibody or the antigen-binding fragment thereof according to any of the above (1) to (4).

(6) A pharmaceutical composition for use in treating cancer, comprising the antibody or the antigen-binding fragment thereof according to the above (4).

(7) A method for predicting an antitumor effect of an antibody or an antibody-drug conjugate (ADC), comprising:
evaluating an ability of the ADC to penetrate into the inside of a solid tumor; and
predicting that the ADC has a high antitumor effect when the ADC penetrates into the inside of the solid tumor.

(8) A method for predicting an ability of an antibody or an antibody-drug conjugate (ADC) to penetrate into the inside of a solid tumor, comprising:
determining an association rate constant Ka and a dissociation rate constant Kd for binding of the ADC or the antibody or an antigen-binding fragment thereof constituting the ADC to an antigen; and
predicting that the ADC has a high ability to penetrate into the inside of the solid tumor when the association rate constant Ka is not less than a first predetermined value and the dissociation rate constant Kd is not less than a second predetermined value.

(9) A method for predicting an antitumor effect of an antibody or an antibody-drug conjugate (ADC), comprising:
determining an association rate constant Ka and a dissociation rate constant Kd for binding of the ADC or the antibody or an antigen-binding fragment thereof constituting the ADC to an antigen; and
predicting that the ADC has a high antitumor effect when the association rate constant Ka is not less than a first predetermined value and the dissociation rate constant Kd is not less than a second predetermined value.

BRIEF DESCRIPTION OF DRAWINGS

FIG. 1 shows the sensorgram to which an approximate curve was curve-fitted by using a kinetic titration 1:1 interaction model. In FIGS. 1 to 3, "1084ADC" refers to an ADC composed of a monoclonal antibody produced by clone No. 1084 and monomethyl auristatin E, and "1849ADC" refers to an ADC composed of a monoclonal antibody produced by clone No. 1849 and monomethyl auristatin E. "Dissociation phase" in the figure represents the state wherein only flow buffer is flowed and dissociation of the antibody from the antigen thereof is observed.

FIG. 2 is a graph that shows an antitumor effect of 1084ADC and 1849ADC on a tumor-bearing model based on change in tumor size after administration thereof.

FIG. 3 is a set of fluorescent microscopy photos that show penetration of 1084ADC and 1849ADC into the inside of a solid tumor.

DETAILED DESCRIPTION OF THE INVENTION

Figure 1:
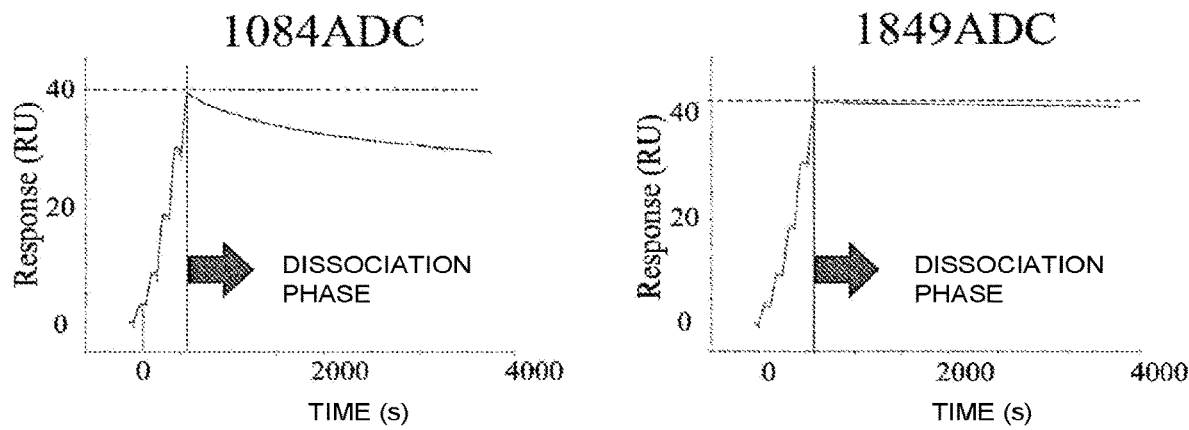
FIG. 1 is a sensorgram obtained from SPR measurement of binding of an antibody-drug conjugate (ADC) to an immobilized antigen.

In the present invention, "subject" refers to a mammal, and particularly, a subject may be a human.

As used herein, "treatment" refers to treating, curing, preventing, or improving remission of a disease or a disorder, or decreasing the rate of progression of the disease or the disorder.

As used herein, "disease" refers to a symptom for which treatment is beneficial.

As used herein, "therapeutically effective amount" refers to an amount of a pharmaceutical agent effective to manage (prevent or treat) a disease or a condition. A therapeutically effective amount of the pharmaceutical agent can reduce the rate of deterioration of a symptom of the disease or the condition, stop deterioration of the symptom, ameliorate the symptom, cure the symptom, or inhibit the onset or development of the symptom.

As used herein, "antibody" refers to an immunoglobulin, which is a protein having a structure stabilized by disulfide bonds in which two heavy chains (H chains) and two light chains (L chains) are linked together. A heavy chain consists of a heavy chain variable region VH, heavy chain constant regions CH1, CH2, and CH3, and a hinge region between CH1 and CH2, and a light chain consists of a light chain variable region VL and a light chain constant region CL. Among these regions, a variable region fragment (Fv) consisting of VH and VL is a region that is directly responsible for antigen binding and confers variability to the antibody. An antigen binding region consisting of VL, CL, VH, and CH1 is referred to as a Fab region, and a region consisting of the hinge region, CH2, and CH3 is referred to as a Fc region.

A region that is a part of the variable regions and comes into direct contact with an antigen especially varies greatly and is referred to as a complementarity-determining region (CDR). A relatively less variable part other than CDR is referred to as a framework region (FR). Each of the light chain variable region and the heavy chain variable region has three CDRs and respective CDRs are referred to as heavy chain CDRs 1 to 3 and light chain CDRs 1 to 3, sequentially from N-terminus.

The antibody may be a recombinant antibody, or may be a chimeric antibody, a humanized antibody, or a fully humanized antibody. The antibody is preferably a monoclonal antibody. A chimeric antibody is an antibody having a heavy chain variable region and a light chain variable region from one species linked to a heavy chain constant region and a light chain constant region from a different species, respectively. A humanized antibody refers to an antibody in which an amino acid sequence characteristic of an antibody derived from a non-human has replaced a corresponding position of a human antibody. Examples of the humanized antibody include an antibody having heavy chain CDRs 1 to 3 and light chain CDRs 1 to 3 derived from an antibody produced by immunizing a mouse or a rat and in which all other regions comprising respective four framework regions (FRs) of the heavy chain and the light chain are derived from a human antibody. Such an antibody may be referred to as a CDR-grafted antibody. The term "humanized antibody" may include a human chimeric antibody. A "human chimeric antibody" is an antibody based on an antibody derived from a non-human in which a constant region of the antibody derived from a non-human has been replaced with a constant region of a human antibody. For increasing the ADCC activity of the human chimeric antibody, for example, the subtype of the human antibody used for the constant region can be IgG1. Furthermore, for enhancing cytotoxicity of an antibody, the antibody may be used in the form of an antibody-drug conjugate.

As used herein, "natural antibody" refers to an intact antibody obtained by immunizing an animal (for example, an antibody having two full-length light chains and two full length heavy chains). In the present invention, "naked antibody" refers to an antibody that is not linked to a cytotoxic agent.

Antibodies can be produced as recombinant proteins by animal cells such as Chinese hamster ovary cells (CHO cells).

As used herein, "antigen-binding fragment" refers to an antibody fragment, wherein the fragment binds to tissue factor. Specifically, examples of the antigen-binding fragment include, but are not limited to, Fab consisting of VL, VH, CL, and CH1 regions; Fab' comprising a Fab fragment and a hinge; F(ab')$_2$ comprising two Fabs that are linked together by disulfide bonds in the hinge region; Fv consisting of VL and VH; scFv, which is a single-chain antibody comprising VL and VH linked via an artificial polypeptide linker; as well as a bispecific antibody such as a diabody format, an scDb format, a tandem scFv format, and a leucine zipper format.

As used herein, "tissue factor" is a protein that is one of the blood coagulation factors and is also referred to as thromboplastin. Tissue factor is a transmembrane glycoprotein and known as an initiation factor in extrinsic blood coagulation reaction. Preferably, the tissue factor is a human tissue factor. The amino acid sequence of the human tissue factor is, for example, as shown in NCBI Reference Sequence ID: P #001984.1.

As used herein, "association rate constant" (ka) and "dissociation rate constant" (kd) are rate constants for binding dissociation reaction of two molecules. ka and kd are constants well known to those skilled in the art and can be determined by using a well-known technique such as a surface plasmon resonance method as appropriate.

"Surface plasmon resonance measurement" (SPR measurement) is a method for measuring interaction between substances that utilizes the following phenomenon. That is, when a planar metal/liquid interface is irradiated with polarized light at a certain incidence angle, a part having a decreased reflected light intensity (lost light) appears in the reflected light and the angle thereof varies depending on the amount of substances having bound to the interface. It has been confirmed that 1 RU corresponds to 1 pg/mm$^2$ protein, when a shift in angle of 0.1 degrees of the lost light is defined as 1000 RU.

As used herein, "antibody-drug conjugate" (ADC) refers to a substance composed of an antibody and a drug that are linked to each other. In an ADC, a monoclonal antibody or an antigen-binding fragment thereof may be favorably used as an antibody. In the ADC, the monoclonal antibody and a drug can be linked via a suitable linker. The ADC binds to a membrane component on a cell membrane (e.g., a transmembrane protein such as a receptor) and is brought into the cell by endocytosis and/or internalization, and the drug is cut off from the antibody and released within the cell. Introduction of a cleavable linker between the antibody and the drug in the cell allows for the drug to be separated from the antibody and released into the cytoplasm by cleaving the linker in the cell, for example within an endosome. Using a cytotoxic agent as the drug allows for killing cells to which the drug was delivered. A chemotherapeutic agent, a radioisotope, and a toxin can be used as the cytotoxic agent.

According to past studies, an antibody that binds strongly to a target molecule and does not easily dissociate therefrom has been considered more suitable for therapeutic application. However, in contrast to this, the present invention indicates that an anti-tissue factor antibody, an antibody with a larger dissociation rate constant kd (an antibody that easily dissociates from the tissue factor) has a higher penetrability into a tumor tissue positive for the tissue factor than an antibody with a smaller kd (an antibody that does not easily dissociate) and can penetrate into the inside of the tumor. Based on this finding, the present inventors invented an antibody that penetrates into the inside of a tumor, an ADC composed of such an antibody and a drug, and a pharmaceutical composition for use in treating cancer, comprising the antibody or the ADC.

The present invention provides an antibody that binds to tissue factor, wherein a dissociation rate constant kd thereof is not less than a first specified value and an association rate constant ka thereof is not less than a second specified value. The first specified value may be $1 \times 10^{-4}$ $s^{-1}$ or more, $2 \times 10^{-4}$ $s^{-1}$ or more, $3 \times 10^{-4}$ $s^{-1}$ or more, $4 \times 10^{-4}$ $s^{-1}$ or more, $5 \times 10^{-4}$ $s^{-1}$ or more, $6 \times 10^{-4}$ $s^{-1}$ or more, $7 \times 10^{-4}$ $s^{-1}$ or more, or $8 \times 10^{-4}$ $s^{-1}$ or more. The second specified value may be $1 \times 10^{-4}$ $M^{-1}$ $s^{-1}$ or more, $1.5 \times 10^{-4}$ $M^{-1}$ $s^{-1}$ or more, or $2 \times 10^{-4}$ $M^{-1}$ $s^{-1}$ or more. KD of the antibody may be 1 nM to 100 nM, 10 nM to 50 nM, 20 nM to 40 nM, or 30 nM to 40 nM.

Combinations of the first specified value and the second specified value are as follows: the second specified value may be $1 \times 10^{-4}$ or more and the first specified value may be $1 \times 10^{-4}$ $s^{-1}$ or more; the second specified value may be $1.5 \times 10^{-4}$ $M^{-1}$ $s^{-1}$ or more and the first specified value may be $2 \times 10^{-4}$ $s^{-1}$ or more; or the second specified value may be $2 \times 10^{-4}$ $M^{-1}$ $s^{-1}$ or more and the first specified value may be $3 \times 10^{-4}$ $s^{-1}$ or more. The upper limit of ka and kd may be within the range of ka and kd of antibodies obtained by immunizing an animal.

The present invention provides an antibody that binds to tissue factor, wherein a dissociation rate constant kd thereof is $5 \times 10^{-4}$ or more and an association rate constant ka thereof is $1 \times 10^{4}$ $M^{-1}$ $s^{-1}$ or more. The dissociation rate constant kd may be, for example, $1 \times 10^{-4}$ $s^{-1}$ or more, $2 \times 10^{-4}$ $s^{-1}$ or more, $3 \times 10^{-4}$ $s^{-1}$ or more, $4 \times 10^{-4}$ $s^{-1}$ or more, $5 \times 10^{-4}$ $s^{-1}$ or more, $6 \times 10^{-4}$ $s^{-1}$ or more, $7 \times 10^{-4}$ $s^{-1}$ or more, or $8 \times 10^{-4}$ $s^{-1}$ or more. The association rate constant ka may be $1 \times 10^{-4}$ $M^{-1}$ $s^{-1}$ or more, $1.5 \times 10^{-4}$ $M^{-1}$ $s^{-1}$ or more, or $2 \times 10^{-4}$ $M^{-1}$ $s^{-1}$ or more. KD may be 1 nM to 100 nM, 10 nM to 50 nM, 20 nM to 40 nM, or 30 nM to 40 nM. Particularly, combinations of Ka and Kd are as follows: Ka may be $1 \times 10^{-4}$ $M^{-1}$ $s^{-1}$ or more and Kd may be $1 \times 10^{-4}$ $s^{-1}$ or more; Ka may be $1.5 \times 10^{-4}$ $M^{-1}$ $s^{-1}$ or more and Kd may be $2 \times 10^{-4}$ $s^{-1}$ or more; or Ka may be $2 \times 10^{-4}$ $M^{-1}$ $s^{-1}$ or more and Kd may be $3 \times 10^{-4}$ $s^{-1}$ or more. The antibody having the association rate constant and the dissociation rate constant binds to tissue factor rapidly and also dissociates from the tissue factor rapidly. The upper limit of ka and kd may be within the range of ka and kd of antibodies obtained by immunizing an animal.

Each of the association rate constant ka and the dissociation rate constant kd of an antibody can be determined for example by SPR measurement. SPR measurement for binding between an antibody and an antigen is well known and those skilled in the art will be able to calculate the association rate constant ka and the dissociation rate constant kd of the antibody based on a well-known technique. In SPR measurement, the association rate constant can be calculated from variation of RU in a phase in which an analyte is flowed at a fixed concentration (association phase) and then, the dissociation constant can be calculated from variation of RU in a phase in which running buffer is flowed (dissociation phase). Measurement can be performed by using single-cycle kinetics. Analysis can be performed by bivalent analysis. Curve fitting of an approximate curve to a measured SPR sensorgram can be performed by using a kinetic titration 1:1 interaction model. For details of curve fitting, one can see Karlsson, R., Katsamba, P. S., Nordin, H., Pol, E. and Myszka, D. G. (2006). "Analyzing a kinetic titration series using affinity biosensors." Anal. Biochem. 349 (1): 136-47.

The association rate constant ka and the dissociation rate constant kd of an antibody can also be determined by using an SPR instrument such as Biacore™ commercially available from GE Healthcare according to the manufacturer's manual. For example, the SPR measurement instrument also includes a program for determining ka and kd and can calculate ka and kd from an SPR sensorgram. For example, an SPR sensorgram obtained by a Biacore™ instrument can be subjected to analysis in which Biacore T200 evaluation software is used and a bivalent analyte model is adopted as a fitting model, thereby deriving a fitting curve, from which ka, kd, and KD as kinetics parameters of an antibody or an ADC can be calculated.

Those skilled in the art may produce an antibody having the dissociation rate constant and/or the association rate constant described above by using a well-known conventional technique.

Examples of an antibody that binds to tissue factor, wherein a dissociation rate constant kd thereof is $5 \times 10^{-4}$ $s^{-1}$ or more and an association rate constant ka thereof is $1 \times 10^{4}$ $M^{-1}$ $s^{-1}$ or more, include, but are not particularly limited to, an antibody that binds to tissue factor, wherein the antibody comprises:

a heavy chain variable region comprising CDRs 1 to 3 having an amino acid sequence of SEQ ID NOs: 2 to 4, respectively; and a light chain variable region comprising CDRs 1 to 3 having an amino acid sequence of SEQ ID NOs: 6 to 8, respectively; and an antibody that binds to tissue factor, wherein the antibody comprises:

a heavy chain variable region having an amino acid sequence of SEQ ID NO: 1; and a light chain variable region having an amino acid sequence of SEQ ID NO: 5.

A competitive assay can be used to test whether antibodies have binding properties similar to each other. An antibody that competes with a certain antibody for binding to an antigen thereof can be identified for example by a competitive assay well known to those skilled in the art. When an antibody can block binding of a desired antibody to an antigen thereof, for example, by at least 20%, preferably at least 20 to 50%, further preferably at least 50%, more preferably 60%, more preferably 70%, more preferably 80%, and especially preferably 90% or more in the competitive assay, the antibody can be identified as an antibody that competes for binding to the same antigen. A competitive antibody can be identified by a cross-blocking assay, and preferably a competitive ELISA assay. In the cross-blocking assay, an antigen is coated onto, for example, a microtiter plate, and a competitive antibody entity as a candidate is added thereto and incubated to allow binding between the antigen and the candidate antibody to form. Subsequently, the desired antibody is labelled, then added additionally to the well, incubated, and washed. One can determine whether the candidate antibody competed or not by quantifying the amount of the bound of the desired antibody. When competition exists, the amount of the label remaining in the well should be decreased.

Generally, in the competitive assay, the fact that antibody A causes dissociation of binding of antibody B to an antigen does not always mean that antibody B causes dissociation of binding of antibody A to the antigen. This can be easily understood by imagining a case where antibody A shows extremely strong binding to the antigen compared to antibody B. Identification of an antibody having a similar binding property may be achieved by confirming that antibody A causes dissociation of binding of antibody B to an antigen and antibody B causes dissociation of binding of antibody A to the antigen. Herein, such a competitive state is referred to as "antibody A and antibody B mutually compete with each other for binding to an antigen."

According to the present invention, an antibody that mutually competes with an antibody obtained from clone No. 1084 for binding to tissue factor is considered to have a similar binding activity to the antibody obtained from clone No. 1084. The binding property of the antibody may be defined by a heavy chain variable region and a light chain variable region thereof, and particularly heavy chain CDRs 1 to 3 and light chain CDRs 1 to 3. Therefore, the present invention provides:

an antibody that mutually competes with the antibody obtained from clone No. 1084 for binding to tissue factor;

an antibody that mutually competes, for binding to tissue factor, with an antibody comprising:

a heavy chain variable region comprising CDRs 1 to 3 having an amino acid sequence of SEQ ID NOs: 2 to 4, respectively; and a light chain variable region comprising CDRs 1 to 3 having an amino acid sequence of SEQ ID NOs: 6 to 8, respectively; and an antibody that mutually competes, for binding to tissue factor, with an antibody comprising:

a heavy chain variable region having an amino acid sequence of SEQ ID NO: 1; and a light chain variable region having an amino acid sequence of SEQ ID NO: 5.

The present invention provides an ADC of the antibody or the antigen-binding fragment thereof according to the present invention and a drug. In the ADC according to the present invention, the antibody or the antigen-binding fragment thereof and the drug (e.g., a cytotoxic agent) may be linked via a linker. Examples of the cytotoxic agent for the ADC according to the present invention include a chemotherapeutic agent (e.g., an anticancer drug such as a commercially available anticancer drug, for example, an auristatin (auristatin E, auristatin F phenylenediamine (AFP), monomethyl auristatin E, monomethyl auristatin F, and a derivative thereof), maytansinoids DM1 and DM4, and a derivative thereof), camptothecin (SN-38, topotecan and exatecan, and a derivative thereof), a DNA minor groove binding agent (enediyne, lexitropsin, duocarmycin, and a derivative thereof), a taxane (paclitaxel and docetaxel, and a derivative thereof), a polyketide (discodermolide and a derivative thereof), an anthraquinone type agent (mitoxantrone and a derivative thereof), benzodiazepine (pyrrolobenzodiazepine, indolinobenzodiazepine, and oxazolidinobenzodiazepine, and a derivative thereof), a vinca alkaloid (vincristine, vinblastine, vindesine, and vinorelbine, and a derivative thereof), doxorubicins (doxorubicin, morpholino-doxorubicin, and cyanomorpholino-doxorubicin, and a derivative thereof), a cardiac glycoside (digitoxin and a derivative thereof), calicheamicin, epothilone, cryptophycin, cemadotin, cemadotin, rhizoxin, netropsin, combretastatin, eleutherobin, etoposide, T67 (Tularik), and nocodazole), a radioisotope (e.g., $^{32}$P, $^{60}$C, $^{90}$Y, $^{111}$In, $^{131}$I, $^{125}$I, $^{153}$Sm, $^{186}$Re, $^{188}$Re, and $^{212}$Bi), and a toxin (e.g., diphtheria toxin A, *Pseudomonas* endotoxin, a lysin, and saporin). These can be used as the cytotoxic agent in the ADC according to the present invention. Any cytotoxic agent used for managing cancer can be used.

In an aspect of the present invention, the linker may be a noncleavable linker or a cleavable linker. The antibody and the linker can be joined for example by linking the linker to a sulfhydryl group of the antibody via a maleimide group. The linker may comprise a polyethylene glycol block as necessary.

Examples of the cleavable linker include a peptide linker such as a valine-citrulline (Val-Cit) linker and a phenylalanine-lysine (Phe-Lys) linker, and a hydrazone linker that is cleaved pH-dependently. Further examples of the cleavable linker include linkers comprising a carbamate bond or an ester bond, and these may be decomposed enzymatically in a cell. These linkers may be used in combination.

In an aspect of the present invention, the antibody and the cytotoxic agent can be linked by a maleimide group-PEG-Val-Cit. In an aspect of the present invention, the linker used in Examples of the present application (e.g., a maleimide group-PEG-Val-Cit-PABA-a cytotoxic agent) can be used.

Furthermore, a spacer may intervene between the linker and the cytotoxic agent.

The present invention provides a pharmaceutical composition for use in treating cancer, comprising the antibody or the antigen-binding fragment thereof, or the antibody-drug conjugate (ADC) thereof with a cytotoxic agent according to the present invention.

Examples of the cancer to be treated with the pharmaceutical composition according to the present invention include a solid tumor. Further examples of the cancer to be treated with the pharmaceutical composition according to the present invention include lymphoma, lung cancer, pancreas cancer, head and neck cancer, prostate cancer, bladder cancer, breast cancer, esophageal cancer, stomach cancer, colon cancer, uterine cancer, ovarian cancer, skin cancer, thyroid cancer, thymic carcinoma, renal cancer, testicular cancer, penile cancer, liver cancer, biliary tract cancer, brain tumor, bone and soft tissue tumor, retroperitoneal tumor, angiosarcoma and lymphangiosarcoma, and a metastatic cancer thereof (e.g., metastatic solid tumor). For example, the cancer to be treated with the pharmaceutical composition according to the present invention may be brain tumor, pancreas cancer, breast cancer, or stomach cancer. Especially in the solid tumor, the antibody or the antigen-binding fragment thereof, or the antibody-drug conjugate (ADC) thereof with a cytotoxic agent according to the present invention can penetrate into the inside of a tumor mass and kill or damage internal cancer cells.

The pharmaceutical composition according to the present invention may comprise an excipient in addition to the antibody or the antigen-binding fragment thereof, or the antibody-drug conjugate (ADC) thereof with a cytotoxic agent according to the present invention. Example of the excipient includes buffer. The pharmaceutical composition according to the present invention can be administered by intravenous administration, intraperitoneal administration, and the like. The pharmaceutical composition according to the present invention may be in the form of an injection, for example, in the form stored in a syringe.

The present invention provides a method for treating cancer in a subject in need thereof, comprising administering a therapeutically effective amount of the antibody or the antigen-binding fragment thereof, or the antibody-drug conjugate (ADC) thereof with a cytotoxic agent according to the present invention to the subject.

The present invention provides use of the antibody or the antigen-binding fragment thereof, or the antibody-drug conjugate (ADC) thereof with a cytotoxic agent according to the present invention, in manufacturing a medicament for use in treating cancer.

EXAMPLES

Example 1: Obtaining Antibodies that Bind to Tissue Factor

In this example, an anti-tissue factor antibody was obtained and the amino acid sequence thereof was determined.

Immunization Method

Recombinant human tissue factor micellized using FCA adjuvant (rhTF, SEQ ID NO: 13) was intraperitoneally administered to Wister rats. After several immunizations, rat antisera were examined by ELISA using a solid phase having rhTFs thereon. A spleen was excised from a rat individual that had shown an increased antibody titer and splenocytes were obtained therefrom. The splenocytes and p3X63 mouse myeloma cells were fused by a PEG technique and cultivated in a HAT culture medium to select hybridoma cells. The hybridoma cells were screened to select those that reacted positively to rhTFs in ELISA and also reacted positively to cells expressing human tissue factor strongly such as an MCF7 cell in flow cytometry analysis. The selected hybridoma cells were cloned by limiting dilution to establish hybridoma cell clones that produced anti-tissue factor antibodies.

From the resulting hybridoma clones, clone No. 1084 and clone No. 1849 that produced anti-tissue factor antibodies were collected and total RNA was extracted from each clone according to a routine method. Subsequently, cDNA was synthesized by using SMARTer RACE 5'/3' Kit (Takara Bio Inc.).

PCR was performed by using the synthesized cDNA as a template, thereby amplifying DNA sequences that encoded variable regions of the heavy chain and the light chain of No. 1084 and No. 1849. For the PCR reaction, 10× Universal Primer A Mix (SMARTer RACE 5'/3' Kit, Takara Bio Inc.) was used as a sense primer, and primer sequences shown below for each of the heavy chain and the light chain were used as a reverse primer.

TABLE 1

Table 1: Used Primer Sequences

| Name of primers | Nucleic acid sequence | Sequence number |
|---|---|---|
| 10 × Universal Primer A Mix, Long (0.4 µM) | CTAATACGACTCACTATAGGGCA AGCAGTGGTATCAACGCAGAGT | 9 |
| 10 × Universal Primer A Mix, Short (2 µM) | CTAATACGACTCACTATAGGGC | 10 |
| Reverse primer for heavy chain | TGTGCAGACCCTCGTGGACCACG GAGCA | 11 |
| Reverse primer for light chain | CCTTAGGAGGGAAGATTGGAAGG AGCT | 12 |

Each PCR product obtained above was cloned into a vector and the base sequence thereof was determined according to a routine method. Consequently, it was found that the monoclonal antibody produced by clone No. 1084 had a base sequence and an amino acid sequence shown in the table below.

Formula 1
DNA sequence and amino acid sequence of heavy chain variable region of antibody 1084

```
         10        20        30        40        50        60
CAGGTGCAGCTGAAGGAGTCAGGACCTGGTCTGGTGCAGCCCTCACAGACCCTGTCCCTC
 Q  V  Q  L  K  E  S  G  P  G  L  V  Q  P  S  Q  T  L  S  L 70        80        90       100       110       120
ACCTGCATTGTCTCTGGATTCTCACTAACTAACTACAATGTGCACTGGGTTCGACAGCCT
 T  C  I  V  S  G  F  S  L  T [N  Y  N  V  H] W  V  R  Q  P
                               H-CDR1

130       140       150       160       170       180
GCAGGAGCAGGTCTGGAGTGGATGGGAGTAATTTGGACTGATGGAAAAACAGATTACAAT
 A  G  A  G  L  E  W  M  G [V  I  W  T  D  G  K  T  D  Y  N
                                               H-CDR2

190       200       210       220       230       240
TCAACTCTCCAATCCCGACTGAGCATCAGCAGGGACACCTCCAAGAGCCAAGTTTTCTTA
 S  T  L  Q  S] R  L  S  I  S  R  D  T  S  K  S  Q  V  F  L 250       260       270       280       290       300
AAAATGAACAGTCTGCAAGCTGAGGACATAGCCACTTACTACTGTGCCAGAGATTGGGAT
 K  M  N  S  L  Q  A  E  D  I  A  T  Y  Y  C  A  R [D  W  D
                                                     H-CDR3
```

-continued
```
          310          320          330          340
ACCGGCTTTGATTACTGGGGCCAAGGAGTCATGGTCACAGTCTCCTCA
 T  G  F  D  Y | W  G  Q  G  V  M  V  T  V  S  S
```

Correspondence between the above described amino acid sequence and sequence numbers in Sequence Listing is as follows.
SEQ ID NO: 1: the amino acid sequence of the heavy chain variable region of antibody 1084,
SEQ ID NO: 2: the amino acid sequence of the heavy chain CDR1 of antibody 1084,
SEQ ID NO: 3: the amino acid sequence of the heavy chain CDR2 of antibody 1084,
SEQ ID NO: 4: the amino acid sequence of the heavy chain CDR3 of antibody 1084.

Formula 2
DNA sequence and amino acid sequence of light chain variable region of antibody 1084

```
          10           20           30           40           50           60
GACATCAAGATGACCCAGTCTCCCTCCTCCCTGTCTGCATCTCTGGGAGAAAGAGTCACC
 D  I  K  M  T  Q  S  P  S  S  L  S  A  S  L  G  E  R  V  T 70           80           90          100          110          120
ATCAGTTGCAGGGCAAGTGAGAATATTAACAATATTTTGGCCTGGTATCAGAAGAAAGAA
 I  S  C |R  A  S  E  N  I  N  N  I  L  A | W  Y  Q  K  K  E
          L-CDR1

130          140          150          160          170          180
GATGGAAGTGTTAAACTCCTGATTCACTACACATCAAATCTACAATCTGGGGTCCCATCA
 D  G  S  V  K  L  L  I  H |Y  T  S  N  L  Q  S | G  V  P  S
                             L-CDR2

190          200          210          220          230          240
AGGTTCAGTGGCAGTGGGTCTGGGAAAGATTACTCTCTTACCATTAGTGGCCTAGAATCT
 R  F  S  G  S  G  S  G  K  D  Y  S  L  T  I  S  G  L  E  S 250          260          270          280          290          300
GAAGATATTGCGACTTACTATTGTCAGCAGGCTTATACCCCGTACGCGTTTGGAGCTGGG
 E  D  I  A  T  Y  Y  C |Q  Q  A  Y  T  P  Y  A | F  G  A  G
                          L-CDR3

310
ACCAAGCTGGAACTGAAA
 T  K  L  E  L  K
```

Correspondence between the above described amino acid sequence and sequence numbers in Sequence Listing is as follows.
SEQ ID NO: 5: the amino acid sequence of the light chain variable region of antibody 1084,
SEQ ID NO: 6: the amino acid sequence of the light chain CDR1 of antibody 1084,
SEQ ID NO: 7: the amino acid sequence of the light chain CDR2 of antibody 1084,
SEQ ID NO: 8: the amino acid sequence of the light chain CDR3 of antibody 1084.

The CDRs 1 to 3 of the heavy chain variable region and the CDRs 1 to 3 of the light chain variable region of No. 1084 were sequenced by comparing the amino acid sequences of the heavy chain variable region and the light chain variable region described above with database of amino acid sequences of known antibodies (IMGT website: http://www.imgt.org/) and investigating homology.

Example 2: Production of Antibody-Drug Conjugate (ADC)

In this example, an antibody-drug conjugate composed of the obtained monoclonal antibody and a cytotoxic agent was produced.

In this example, monomethyl auristatin E (hereinafter referred to as "MMAE") was used as a cytotoxic agent. Conjugation of the antibody and the cytotoxic agent was performed as described below.

First, buffer for used in a reduction process was prepared. A Dulbecco's phosphate buffered saline (DPBS) containing 5 mM EDTA (pH 8.0) was prepared as buffer A, and a solution containing 100 mM sodium dihydrogenphosphate, 150 mM sodium chloride, and 5 mM EDTA (pH 8.0) was prepared as buffer B. A solution of a reducing agent was prepared by dissolving mercaptoethylamine hydrochloride salt (Sigma-Aldrich Corporation) as the reducing agent in buffer A.

Second, an antibody solution was prepared by adding 0.5 M EDTA (pH8.0) to DPBS containing 2 to 5 mg/mL antibodies such that the final concentration of EDTA became 5 mM.

The amount of solution to yield the final antibody concentration of 1 mg/mL was the total amount of reaction solution for reduction reaction of antibodies. The antibody solution was mixed with buffer B in an amount of one sixth the total amount of the reaction solution, and finally the final antibody concentration was adjusted to 1 mg/mL by using buffer A. This solution mixture was preincubated in a thermostat bath at 37° C. for 15 minutes. Then, the solution of a reducing agent in an amount of one hundredth the total amount of the liquid mixture was added thereto and incubated in the thermostat bath at 37° C. for 30 minutes. The final concentration of the reducing agent for No. 1084 and No. 1849 was 6.4 mM and 6.5 mM, respectively. After completion of reaction, the sample was promptly transferred onto ice and was buffer exchanged to buffer A by using VIVASPIN TURBO 15 (Sartorius AG, Gottingen, Germany) to remove the reducing agent. Buffer exchange was repeated until the original reaction solution was diluted one million or more times.

Then, the amount of solution to yield the final antibody solution concentration of 0.5 mg/mL was the total amount of reaction solution for conjugation reaction of an agent. Buffer B in an amount of one sixth the total amount of reaction solution, the antibody solution comprising reduced antibodies, and linker-MMAE in 3-fold molar amount relative to free thiol groups were mixed, and the final antibody concentration was adjusted to 0.5 mg/mL by using buffer A. The solution mixture was mixed by inversion, gently stirred, and then allowed to stand at 4° C. for 18 hours.

Example 3: Evaluation of Binding Activity of Obtained Monoclonal Antibody to Antigen In this example, binding activity of the antibody to the antigen thereof was evaluated by a surface plasmon resonance (SPR) method.

An expression vector of human tissue factor (hTF: UniProtKB-P13726) was constructed by insertion of a peptide having residues 33 to 251 in the amino acid sequence of hTF into pET21b (Novagen) to add a His6 tag to the C terminus thereof. The expression vector into which a sequence of interest was incorporated was used to transform *E. coli* BL21 (DE3) (Novagen). The transformed *E. coli* were cultivated up to an OD600 of 0.6 and IPTG (isopropyl β-D-1-thiogalactopyranoside) was added to be a final concentration of 1 mM, and after cultivation for an additional 3 hours, *E. coli* were recovered. Refolding was performed by bacteriolyzing the recovered *E. coli* by lysozyme, solubilizing insoluble components by 8 M urea, carrying out purification on a Ni-NTA column, and then carrying out dialysis with PBS (−). A purified recombinant human tissue factor (rhTF) was identified by electrophoresis and was used as a final sample.

[Formula 3]

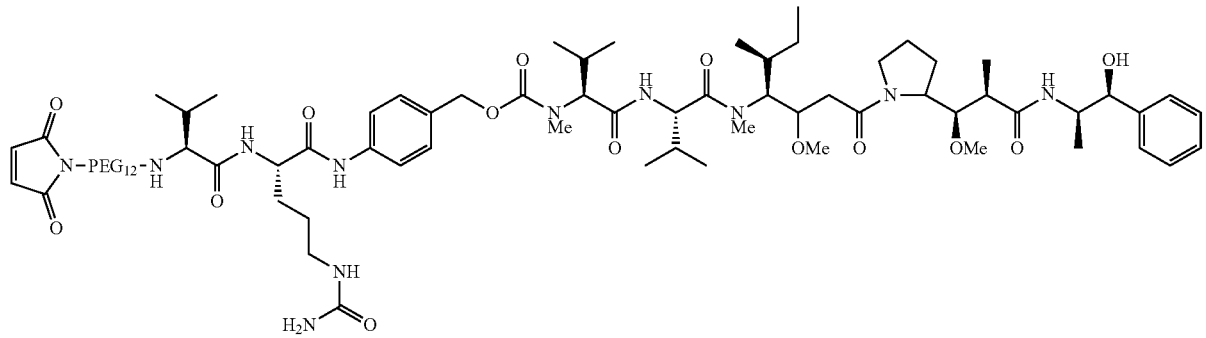

Structure of linker-MMAE used in this example

[wherein $PEG_{12}$ represents polyethylene glycol ($-CH_2-CH_2-O-)_{12}$ and Me represents a methyl group.]

Specifically, the above described linker is a compound in which, from right to left, a maleimide group, PEG, valine-citrulline, para-aminobenzoic acid (PABA), and MMAE are linked. The above described linker can be linked via a maleimide group to a sulfhydryl group that the reduced antibody has.

Finally, VIVASPIN TURBO 15 was used again to exchange buffer to DPBS. Buffer exchange was repeated until the original reaction solution was diluted one million or more times. After the produced ADC was subjected to filtering treatment by using a filter unit with a 0.22 μm PVDF membrane under a sterile condition, the antibody concentration was adjusted to 2 mg/mL by using sterile DPBS and samples were divided, and frozen and stored at −80° C. until use. Freezing was only performed once and the samples were used for each experiment promptly after freeze-thawing. The ADC comprising the antibody produced by clone No. 1084 is referred to as 1084ADC and the ADC comprising the antibody produced by clone No. 1849 is referred to as 1849ADC.

SPR measurement was performed by using BiaCore T200 (GE Healthcare). The recombinant human tissue factor antigen (rhTF antigen) was subjected to buffer exchange to 10 mM sodium acetate solution (pH 5.0) and the final protein concentration was adjusted to 2 to 10 μg/mL. Subsequently, contact time was set to 30 seconds and the antigen was immobilized on a CM5 sensor chip (GE Healthcare) according to a basic protocol by using amine coupling. Then, 5 dilution series of the antibody solution were prepared by diluting each ADC solution in DPBS so that the final concentrations thereof became 320 nM, 160 nM, 80 nM, 40 nM, and 20 nM. Measurement was performed by using single-cycle kinetics, in which DPBS was used as running buffer for measurement and the contact time and the dissociation time were set to 60 seconds and 3200 seconds, respectively. ka, kd, and KD as kinetics parameters of the antibody or the ADC were calculated by analyzing the measurement result using Biacore T200 evaluation software and adopting a bivalent analyte model as a fitting model, thereby deriving a fitting curve. The association rate constant ka and the dissociation rate constant kd obtained by analysis are shown in Table 2.

TABLE 2

Table 2: evaluation of binding activity of 1084ADC and 1849ADC to rhTF by SPR

|  | Ka (1/Ms × 10$^4$) | Kd (1/s × 10$^{-4}$) | KD (nM) |
| --- | --- | --- | --- |
| 1084ADC | 2.61 ± 0.87 | 8.25 ± 0.64 | 34.96 ± 0.47 |
| 1849ADC | 4.20 ± 1.94 | 0.21 ± 0.09 | 0.54 ± 0.19 |

As is shown in Table 2, regarding binding of 1084ADC to rhTF, the association rate constant (Ka) was (2.61±0.87)× 10$^4$ M$^{-1}$ s$^{-1}$, the dissociation rate constant (Kd) was (8.25±0.64)×10$^{-4}$ s$^{-1}$, and KD was 34.96±0.47 nM. On the other hand, regarding binding of 1849ADC to rhTF, the association rate constant (Ka) was (4.20±1.97)×10$^4$ M$^{-1}$ s$^{-1}$, the dissociation rate constant (Kd) was (0.21±0.09)× 10$^{-4}$ s$^{-1}$, and KD was 0.54±0.19 nM.

Since the association rate constant (Ka) of 1849ADC was 1.61 times that of 1084ADC and the dissociation rate constant (Kd) of 1084ADC was 39.29 times that of 1849ADC, it is believed that the difference of KD value (Kd/Ka) of these ADCs is attributed mainly to Kd. Specifically, it was suggested that 1849ADC had a slow dissociation rate and was less likely to dissociate from the antigen, while 1084ADC had a fast dissociation rate and was more likely to dissociate from the antigen.

Example 4: Evaluation of Antitumor Effect of Produced ADCs

In this example, the antitumor effect of the ADCs whose properties were analyzed as described above was studied.

5 week old female BALB/c-nu/nu mice were subjected to inhalation anesthesia and cell suspension of human pancreatic cancer cell line BxPC3 was subcutaneously injected into the mouse on the right dorsal part in an amount of 100 µL (1×10$^6$ cells)/mouse. The mice were kept and the mice whose tumor size reached about 600 mm$^3$ were used as a model of subcutaneous transplantation of BxPC3 for an experiment. On day 0, day 3, day 7, day 10, day 14, and day 17, wherein the time when treatment was started was considered to be day 0, 5 mg/kg ADC (in terms of protein amount) was administered to the model of subcutaneous transplantation of BxPC3 via tail vein, and after that tumor volume was measured twice a week. Change of the tumor volume is shown in FIG. 2.

Figure 2:
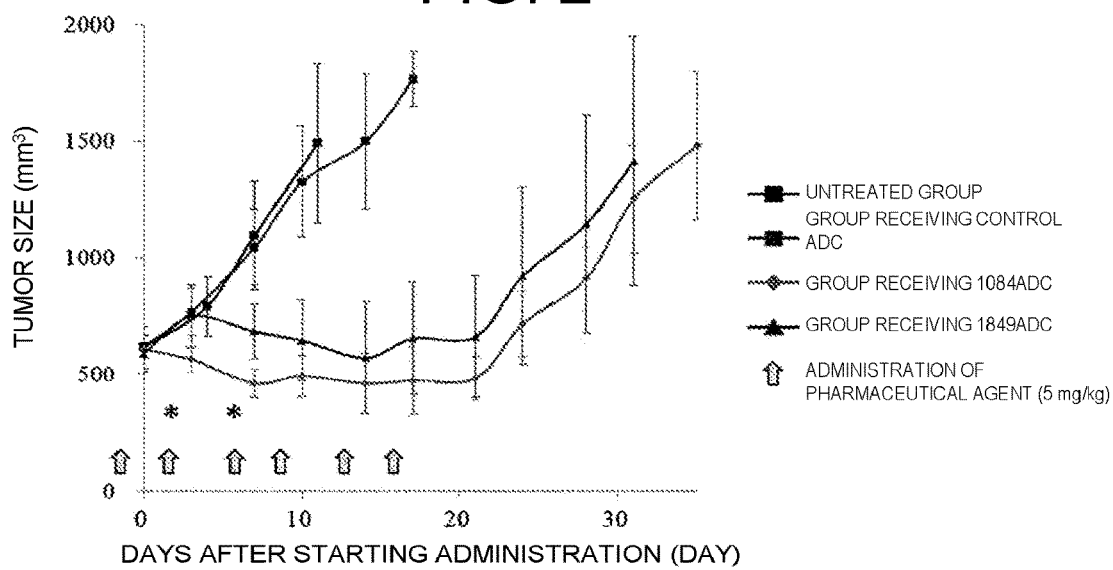

As is shown in FIG. 2, the group receiving 1084ADC and the group receiving 1849ADC showed a significant effect of suppressing tumor growth compared to an untreated group and a group receiving a control ADC. Furthermore, tumor regression was observed immediately after starting administration of the pharmaceutical agent in the group receiving 1084ADC, while tumor regression was observed three or more days after starting administration in the group receiving 1849ADC. There was a statistically significant difference between day 3 and day 7 after starting administration of the pharmaceutical agent (marked with "*" in the figure). (day 3: p<0.05, day 7: p<0.01).

According to Example 3, 1849ADC binds to TF more strongly than 1084ADC, and according to Examples 2 and 3, 1849ADC is less likely to dissociate from TF than 1084ADC. In contrast to this, in this example, 1084ADC had a higher antitumor effect than that of 1849ADC. This result suggests that the efficacy of ADCs cannot be predicted correctly only based on the KD value of the antibody.

Example 5: Intratumoral Distribution of ADCs

In this example, the intratumoral distribution of 1084ADC and 1849ADC after administration thereof was studied.

The mouse obtained by the method of Example 4 was used as a mouse model of subcutaneous transplantation of BxPC3. Each ADC was fluorescently labeled by using Alexa Fluor 647 labeling kit (Thermo Fisher Scientific Inc.). Each fluorescently labeled ADC was administered to the mouse model of subcutaneous transplantation of BxPC3 via tail vein in a dose of 5 mg/kg (in terms of protein amount). 3 hours after administration, the mouse was euthanized and a tumor formed by BxPC3 was excised. The tumor tissue was embedded in Tissue-Tec optimal-cutting-temperature compound (Sakura Finetek) and was frozen and stored at −80° C. Subsequent procedures were performed under protection from light where possible until a fluorescence image was taken.

Next, Leica CM1860 cryostat (Leica Biosystems) was used to prepare 6 µm-thick frozen sections from the frozen tumor tissue and the sections were placed on slide glasses and air-dried for 30 minutes. Then, the tissue sections were fixed by immersing the sections in phosphate buffer containing 4% paraformaldehyde at room temperature for 15 minutes. Subsequently, after the slide glasses were washed three times with DPBS, blocking treatment was performed by applying a blocking solution, in which 5% w/v skimmed milk (Becton, Dickinson and Company) was prepared in DPBS, to the tissue sections and allowing the sections to stand in a humidifier at 4° C. for 18 hours.

After washing out the blocking solution with DPBS, 0.2 mg/mL goat anti-mouse CD31 polyclonal antibody (R&D Systems, Inc.) as a primary antibody was diluted 100-fold in the blocking solution and adequate amounts thereof were applied to the tissue sections, and the tissue sections were allowed to stand in the humidifier at room temperature for one hour.

After washing the slide glasses again with DPBS three times, Alexa FluorR 555 anti-goat polyclonal antibody (Thermo Fisher Scientific Inc.) to be used as a secondary antibody was diluted 500-fold in the blocking solution and adequate amounts thereof were applied to the tissue sections, and the tissue sections were allowed to stand in the humidifier at room temperature for one hour.

Finally, after washing the slide glasses with DPBS three times, adequate amounts of nuclear staining solution prepared by diluting 1 mg/mL DAPI 500-fold in DPBS were applied to the tissue sections, and the tissue sections were allowed to stand in the humidifier at room temperature for 5 minutes to perform nuclear stain. Then, the slide glasses were washed again with DPBS three times and the moisture was removed thoroughly, and then the tissue sections were mounted by using Fluoromount-G and putting micro cover glasses thereon. Immunofluorescent staining images were taken by using a virtual slide system (Olympus Corporation) under the same conditions. The obtained staining images are shown in FIG. 3.

Figure 3:
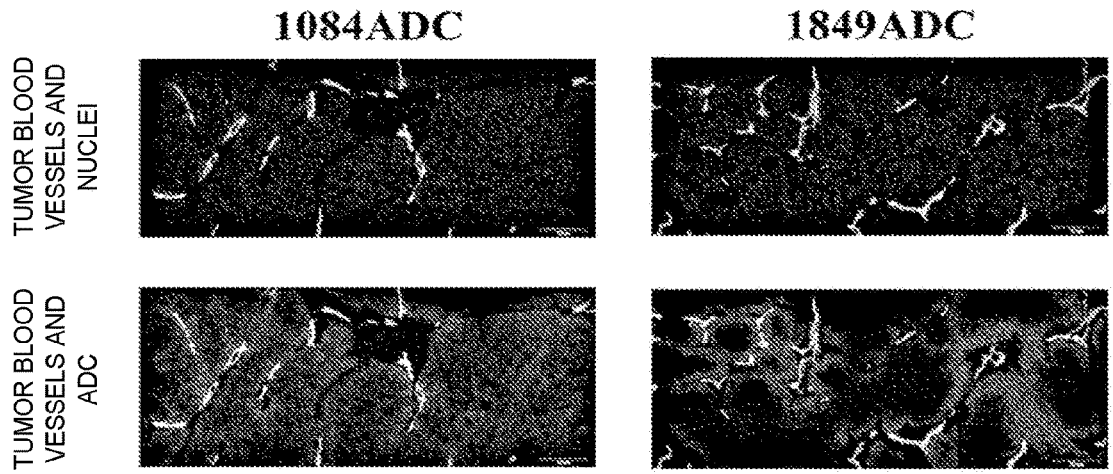

As is shown in FIG. 3, 1084ADC (lower left panel, red) distributed uniformly across the tumor tissue, while 1849ADC (lower right panel, red) distributed near tumor vessels (green) and did not penetrate into the inside of the tumor tissue, suggesting that 1084ADC had a better penetrability into the tumor tissue than 1849ADC.

When considered together with the results of Example 4, the better penetrability into the tumor tissue of 1084ADC compared with 1849ADC was believed to be one of the reasons for the high antitumor effect exhibited by 1084ADC.

The invention claimed is:

1. An antibody that binds to tissue factor, or an antigen-binding fragment thereof, wherein the antibody has a dissociation rate constant Kd of $5\times10^{-4}$ $s^{-1}$ or more and an association rate constant Ka of $1\times10^{4}$ $M^{-1}$ $s^{-1}$ or more, which comprises:
- a heavy chain variable region comprising complementarity-determining regions (CDRs) 1 to 3 having amino acid sequences of SEQ ID NOs: 2 to 4, respectively; and
- a light chain variable region comprising CDR 1 to 3 having amino acid sequences of SEQ ID NOs: 6 to 8, respectively.

2. The antibody or the antigen-binding fragment thereof according to claim 1, which comprises:
- a heavy chain variable region having an amino acid sequence of SEQ ID NO: 1; and
- a light chain variable region having an amino acid sequence of SEQ ID NO: 5.

3. A pharmaceutical composition, comprising the antibody or the antigen-binding fragment thereof according to claim 1, and a diluent or a pharmaceutically acceptable excipient.

4. A pharmaceutical composition, comprising the antibody or the antigen-binding fragment thereof according to claim 2, and a diluent or a pharmaceutically acceptable excipient.

* * * * *